(12) United States Patent
Nie et al.

(10) Patent No.: US 7,588,827 B2
(45) Date of Patent: Sep. 15, 2009

(54) SURFACE ENHANCED RAMAN SPECTROSCOPY (SERS)-ACTIVE COMPOSITE NANOPARTICLES, METHODS OF FABRICATION THEREOF, AND METHODS OF USE THEREOF

(75) Inventors: Shuming Nie, Atlanta, GA (US); William Doering, Mountain View, CA (US)

(73) Assignee: Emory University, Atlanta, GA (US)

( * ) Notice: Subject to any disclaimer, the term of this patent is extended or adjusted under 35 U.S.C. 154(b) by 627 days.

(21) Appl. No.: 10/919,944

(22) Filed: Aug. 17, 2004

(65) Prior Publication Data

US 2009/0140206 A1 Jun. 4, 2009

Related U.S. Application Data

(60) Provisional application No. 60/496,104, filed on Aug. 18, 2003.

(51) Int. Cl.
*B32B 5/66* (2006.01)
(52) U.S. Cl. .................. 428/403; 428/404; 428/405; 428/406; 428/407; 427/212; 436/166; 356/301
(58) Field of Classification Search .............. 428/403, 428/404, 405, 406, 407, 212; 436/166; 356/301
See application file for complete search history.

(56) References Cited

U.S. PATENT DOCUMENTS

| 5,567,628 | A | 10/1996 | Tarcha et al. ............... 436/525 |
| 6,025,202 | A | 2/2000 | Natan ........................ 436/104 |
| 6,149,868 | A | 11/2000 | Natan et al. ............... 422/82.05 |
| 6,174,677 | B1 | 1/2001 | Vo-Dinh ........................ 435/6 |
| 6,219,137 | B1 | 4/2001 | Vo-Dinh ...................... 356/301 |
| 6,242,264 | B1 | 6/2001 | Natan et al. .................. 436/171 |
| 6,344,272 | B1 | 2/2002 | Oldenburg et al. ........... 428/403 |
| 6,514,767 | B1* | 2/2003 | Natan .......................... 436/166 |
| 6,624,886 | B2 | 9/2003 | Natan et al. .................. 356/301 |
| 6,699,724 | B1 | 3/2004 | West et al. ................... 436/525 |

OTHER PUBLICATIONS

Dissertation—Chapters 3-5 Indiana University, Bloomington, Aug. 2003.
William E. Doering and Shuming Nie; Spectroscopic Tags Using Dye-Embedded Nanoparticles and Surface-Enhanced Raman Scattering; Anal. Chem. 2003, 75, 6171-6176.
Dissertation—Chapters 3-5 Indiana University, Bloomington, May 2004.

* cited by examiner

*Primary Examiner*—Leszek Kiliman
(74) *Attorney, Agent, or Firm*—Thomas, Kayden, Horstemeyer & Risley, LLP

(57) ABSTRACT

Nanoparticles, methods of preparation thereof, and methods of detecting a target molecule using embodiments of the nanoparticle, are disclosed. One embodiment of an exemplary nanoparticle, among others, includes a surface-enhanced Raman spectroscopic active composite nanostructure. The surface-enhanced Raman spectroscopic active composite nanostructure includes a core, at least one reporter molecule, and an encapsulating material. The reporter molecule is bonded to the core. The reporter molecule is selected from: an isothiocyanate dye, a multi-sulfur organic dye, a multi-heterosulfur organic dye, a benzotriazole dye, and combinations thereof. The encapsulating material is disposed over the core and the reporter molecule. After encapsulation with the encapsulating material, the reporter molecule has a measurable surface-enhanced Raman spectroscopic signature.

24 Claims, 6 Drawing Sheets

SURFACE ENHANCED RAMAN SPECTROSCOPY (SERS)-ACTIVE COMPOSITE NANOPARTICLES, METHODS OF FABRICATION THEREOF, AND METHODS OF USE THEREOF

CROSS-REFERENCE TO RELATED APPLICATION

This application claims priority to copending U.S. provisional patent application entitled "SURFACE ENHANCED SPECTROSCOPY (SERS)-ACTIVE COMPOSITE NANOPARTICLES, METHODS OF FABRICATION THEREOF, AND METHODS OF USE THEREOF" filed on Aug. 18, 2003 and accorded Ser. No. 60/496,104, which is entirely incorporated herein by reference.

STATEMENT REGARDING FEDERALLY SPONSORED RESEARCH OR DEVELOPMENT

This invention was made with government support under Grant No.: (R01GM58173) awarded by the National Institute of Health and Grant No.: (F49620-02-1-0381) awarded by the Air Force Office of Scientific Research MURI program. The government has certain rights in the invention.

TECHNICAL FIELD

The present disclosure is generally related to surface enhanced spectroscopy and nanoparticles used in surface enhanced Raman spectroscopy.

BACKGROUND

The discovery of single-molecule and single-nanoparticle surface-enhanced Raman scattering (SERS) has attracted considerable interest, both for fundamental studies of enhancement mechanisms and for potential applications in ultrasensitive optical detection and spectroscopy. A number of researchers have shown that the enhancement factors are as large as $10^{14}$-$10^{15}$, leading to Raman scattering cross sections that are comparable to or even larger than those of fluorescent organic dyes. This enormous enhancement allows spectroscopic detection and identification of single molecules located on the surface of single nanoparticles or at the junction of two particles at room temperature. Progress has been made concerning both the structural and mechanistic aspects of single-molecule SERS, but it is still unclear how this large enhancement effect might be exploited for applications in analytical chemistry, molecular biology, or medical diagnostics. One major problem is the intrinsic interfacial nature of SERS, which requires the molecules to adsorb on roughened metal surfaces. For biological molecules such as peptides, proteins, and nucleic acids, surface-enhanced Raman data are especially difficult to obtain, hard to interpret, and nearly impossible to reproduce. Therefore, a need in the industry exists to improve SERS data for biological molecules.

SUMMARY

Nanoparticles, methods of preparation thereof, and methods of detecting a target molecule using embodiments of the nanoparticle, are disclosed. One embodiment of an exemplary nanoparticle, among others, includes a surface-enhanced Raman spectroscopic active composite nanostructure. The surface-enhanced Raman spectroscopic active composite nanostructure includes a core, a reporter molecule, and an encapsulating material. The reporter molecule is bonded to the core. The reporter molecule is selected from: an isothiocyanate dye, a multi-sulfur organic dye, a multi-heterosulfur organic dye, a benzotriazole dye, and combinations thereof. The encapsulating material is disposed over the core and the reporter molecule. The encapsulated reporter molecule has a measurable surface-enhanced Raman spectroscopic signature.

Another embodiment of the nanoparticle, among others, includes a core, at least one reporter molecule, and an encapsulating material. The reporter molecule is disposed on the core, where the reporter molecule covers about 15 to 50% of the surface of the core. The encapsulating material covers the core and the reporter molecule. After encapsulation with the encapsulating material, the reporter molecule has a measurable surface-enhanced Raman spectroscopic signature.

One embodiment of an exemplary method, among others, includes: introducing a core to a reporter molecule, the reporter molecule bonding to the core, wherein the reporter molecule is selected from an isothiocyanate dye, a multi-sulfur organic dye, a multi-heterosulfur organic dye, a benzotriazole dye, and/or combinations thereof; and disposing an encapsulating material onto the core and reporter molecule, wherein after disposing the encapsulating material, the reporter molecule has a measurable surface-enhanced Raman spectroscopic signature.

One embodiment of an exemplary method of detecting a target molecule, among others, includes: attaching a target molecule to a nanostructure as described above; exciting the reporter molecule with a source of radiation; and measuring the surface enhanced Raman spectroscopy spectrum of the nanostructure corresponding to the reporter molecule in order to determine the presence of the target molecule.

BRIEF DESCRIPTION OF THE DRAWINGS

The disclosure can be better understood with reference to the following drawings. The components in the drawings are not necessarily to scale, emphasis instead being placed upon clearly illustrating the principles of the present disclosure.

FIG. 4 illustrates a stability comparison between silica-coated and uncoated gold nanoparticles. The upper image depicts optical absorption spectra of uncoated gold colloids before and after the addition of 0.1 M NaCl. The lower image depicts an optical absorption spectrum of silica-coated gold colloids before and after the addition of 0.1 M NaCl. The lack of spectral changes indicates a high degree of stability.

DETAILED DESCRIPTION

In accordance with the purpose(s) of the present disclosure, as embodied and broadly described herein, embodiments of the present disclosure, in one aspect, relate to surface-enhanced Raman spectroscopic (SERS) active composite nanostructures, methods of fabricating these nanostructures, and methods of using these nanostructures. The SERS active composite nanostructures are distinguishable and can be individually detected. In this regard, the SERS active composite nanostructures can be modified so that the SERS active composite nanostructures interact with certain target molecules, which allow detection of the target molecules. In addition, the SERS active composite nanostructures can be used in encoding systems as well as in multiplexing systems. The SERS active composite nanostructures can be used in many areas such as, but not limited to, flow cytometry, chemical array systems, biomolecule array systems, biosensing, biolabeling, high-speed screening, gene expression studies, protein studies, medical diagnostics, diagnostic libraries, and microfluidic systems.

The SERS active composite nanostructure includes, but is not limited to, a core, a reporter molecule, and an encapsulant material. The reporter molecules are disposed (bonded) onto the core, while the encapsulant material covers and protects the core and reporter molecules. Although not intending to be bound by theory, the core optically enhances the SERS spectrum, while the reporter molecule provides a distinct spectroscopic SERS signature. Disposing the encapsulant material over the core and reporter molecule does not substantially impact the spectroscopic SERS signature of the reporter molecule, while protecting the core and reporter molecules. Unlike other SERS particles, the SERS active composite nanostructure described herein have strong SERS intensities (more than about 10,000 counts with 1 mW laser power in about a second). In some embodiments, the SERS active composite nanostructures have measurable surface-enhanced resonance Raman spectroscopic signatures.

Figure 1:
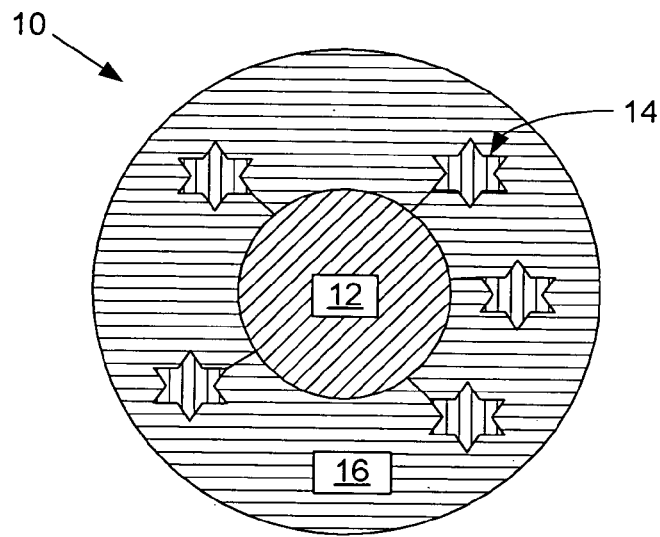
FIG. 1 illustrates a representative embodiment of a SERS active composite nanostructure.

FIG. 1 illustrates a representative embodiment of a SERS active composite nanostructure 10. The SERS active composite nanostructure 10 includes, but is not limited to, a core 12, reporter molecules 14, and an encapsulant material 16. In addition, a coupling agent can be disposed on the core 12 to assist in the bonding between the core 12 and the encapsulant material 16. In an embodiment, the reporter molecules 14 form sulfur-gold bonds that are stable against displacement by the coupling agent and/or the encapsulant material 16 during deposition.

Figure 2A:
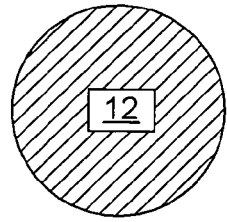
FIGS. 2A through 2C illustrate an embodiment of fabricating the SERS active composite nanostructure shown in FIG. 1.
Figure 2B:
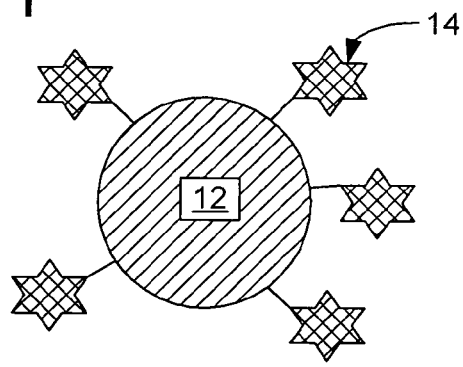
Figure 2C:
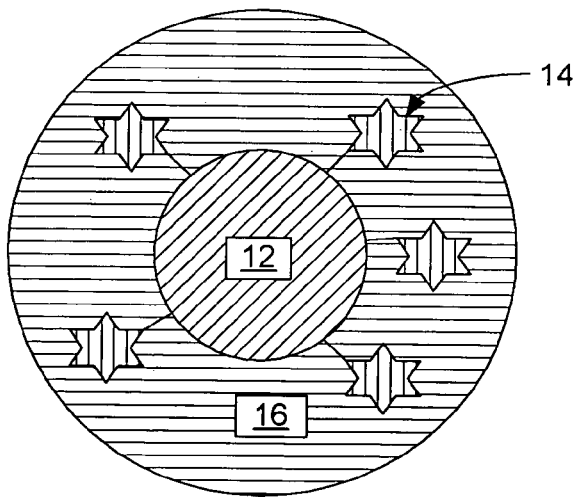

FIGS. 2A through 2C illustrate an embodiment of fabricating the SERS active composite nanostructure 10 shown in FIG. 1. FIG. 2A illustrates the core 12, while FIG. 2B illustrates the core 12 having reporter molecules 14 disposed thereon. FIG. 2C illustrates the encapsulant material 16 disposed over the core 12 and the reporter molecules 14.

The core 12 can be made of materials such as, but not limited to, metals. The core 12 can be a metallic core. In particular, the core 12 can be made of materials such as, but not limited to, gold, silver, copper, transition metals (e.g., Zn, Ni, and Cd), semiconductors (e.g., CdSe, CdS, and InAs), and combinations thereof. In an embodiment, the core 12 can be a gold core.

The reporter molecule 14 can include molecules such as, but not limited to, organic dye molecules having an isothiocyanate group (hereinafter "isothiocyanate dyes"), organic dye molecules having two or more sulfur atoms (hereinafter "multi-sulfur organic dyes"), organic dye molecules having two or more heterocyclic rings each incorporating sulfur atoms (hereinafter "multi-heterosulfur organic dyes"), and benzotriazole dyes. In addition, the reporter molecule 14 includes resonant Raman reporters, which have strong electronic transitions in the visible spectrum, so that resonance Raman enhancement can be used to further amplify the signal intensities. The resonant Raman reporters include, but are not limited to, organic dyes, biomolecules, porphyrins, and metalloporphyrins. In particular, the resonant Raman reporters can include, but are not limited to, malachite green isothiocyanate, tetramethylrhodamine-5-isothiocyante, X-rhodamine-5-isothiocyanate, X-rhodamine-6-isothiocyanate, 3,3'-diethylthiadicarbocyanine iodide, and combinations thereof.

Further, the reporter molecule 14 can include, but is not limited to, thiacyanine dyes, dithiacyanine dyes, thiacarbocyanine dyes (e.g., thiacarbocyanine dyes, thiadicarbocyanine dyes, and thiatricarbocyanine dyes), and dithiacarbocyanine dyes (e.g., dithiacarbocyanine dyes, dithiadicarbocyanine dyes, and dithiatricarbocyanine dyes), and combinations thereof.

Furthermore, the reporter molecule 14 can include: 3,3'-diethyl-9-methylthiacarbocyanine iodide; 1,1'-diethyl-2,2' quinotricarbocyanine iodide; 3,3'-diethylthiacyanine iodide; 4-acetamido-4'-isothiocyanatostilbene-2,2'-disulfonic acid, disodium salt; benzophenone-4-isothiocyanate; 4,4'-diisothiocyanatodihydrostilbene-2,2'-disulfonic acid, disodium salt; 4,4'-diisothiocyanatostilbene-2,2'-disulfonic acid, disodium salt; N-(4-(6-dimethylamino-2-benzofuranyl)phenylisothiocyanate; 7-dimethylamino-4-methylcoumarin-3-isothiocyanate; eosin-5-isothiocyanate; erythrosin-5-isothiocyanate; fluorescein-5-isothiocyanate; (S)-1-p-isothiocyanatobenzyldiethylenetriaminepentaacetic acid; Oregon Green® 488 isothiocyanate; tetramethylrhodamine-5-isothiocyanate; tetramethylrhodamine-6-isothiocyanate; tetramethylrhodamine-5-(and-6)-isothiocyanate; X-rhodamine-5-(and-6)-isothiocyanate, and combinations thereof.

The benzotriazole dyes can include, but are not limited to, azobenzotriazoyl-3,5-dimethoxyphenylamine, and dimethoxy-4-(6'-azobenzotriazolyl)phenol.

As mentioned above, the reporter molecules 14 can have an isothiocyanate group or two or more sulfur atoms (e.g., isothiocyanate dyes, multi-sulfur organic dyes, and multi-heterosulfur organic dyes) that are capable of forming sulfur-gold bonds that are stable against deposition of the coupling agent and the encapsulant material 16. In addition, these reporter molecules 14 have strong electronic transitions in the visible and near-infrared spectra (400-850 nm), so that resonance Raman enhancement can be used to increase signal intensity.

The encapsulating material 16 can include materials such as, but not limited to, silica, polymers, metal oxides, metal sulfides, peptides, proteins, carbohydrates, lipids, nucleic acids, and combinations thereof, as well as salt complexes of each of these. The polymer can include, but is not limited to, synthetic polymers, biopolymers, and combinations thereof. The encapsulating material 16 can include, but is not limited to, streptavidin, avidin, antibodies (secondary and primary), and combinations thereof. The metal oxides can include, but are not limited to, iron oxide, copper oxide, titanium dioxide, metal sulfides thereof, and combinations thereof. In particular, the encapsulating material 16 can include silica.

The SERS active composite nanostructure 10 can have a spherical diameter or substantially spherical diameter of less than about 250 nanometers (nm), about 10 to 150 nm, and about 30 to 90 nm. The core 12 diameter is about 10 to 200 nm, 20 to 100 nm, and 40 to 80 nm. The encapsulant thickness 16 is about 1 to 50 nm, 2 to 50 nm, and 5 to 10 nm. In general, the greater the encapsulant diameter, the better the protection that is provided. With increased diameter, however, the overall size of the SERS active composite nanostructure increases. Selection of the appropriate dimensions can be determined based on the particular application.

In general, the reporter molecule 14 covers from about 1 to 75% of the surface of the core 12 (e.g., the reporter molecule adsorbs onto about 1 to 75% of the core particle surface), about 15 to 50% of the surface of the core 12, about 15 to 30% of the surface of the core 12, and about 20 to 25% of the surface of the core 12.

In embodiments including coupling agents, the coupling agent covers from about 1 to 100% of the surface of the core 12, about 40 to 60% of the surface of the core 12, and about 45 to 50% of the surface of the core 12. The reporter molecule 14 covers from about 1 to 75% of the surface of the core 12, about 15 to 50% of the surface of the core 12, about 15 to 30% of the surface of the core 12, and about 20 to 25% of the surface of the core 12

While the embodiments above have focused on surface enhanced Raman scattering, a number of analogous methods can apply equally well and are included within the scope of the present disclosure. For example, the reporter molecule may be a resonantly-excited reporter molecule, thus making the SERS active composite nanostructure a surface enhanced resonance Raman scattering (SERRS) nanostructure. Likewise, surface enhanced hyperRaman scattering (SEHRS) may also occur at the roughened metal surfaces (as well as the resonant analogue SEHRRS). Indeed, identification of certain SERS active composite nanostructures could rest on a combination of optical interrogation methods, including SERS, SERRS, SEHRS and SEHRRS.

The SERS active composite nanostructure can be prepared in one or more ways. For example, the SERS active composite nanostructure can be prepared by mixing the core with the reporter molecule under conditions such that the reporter molecule bonds to the core. In particular, the core is mixed with reporter molecules having a concentration from about $2.5 \times 10^{-8}$ M to $1.25 \times 10^{-7}$ M and about $7.5 \times 10^{-8}$ M for about 1 to 30 minutes. Then, in an embodiment, a coupling agent is mixed with the core having reporter molecules disposed thereon. In particular, the coupling agent is added to a final concentration of about $2.5 \times 10^{-7}$ M for about 1 to 30 minutes. Subsequently, the core having reporter molecules disposed thereon (and in some embodiments having coupling agents disposed thereon) is mixed with the encapsulating material at a pH of about 9 to 11 for about 24 to 96 hours. Additional details regarding the preparation of the SERS active composite nanostructure are described in Example 1.

In another embodiment of the SERS active composite nanostructure, the encapsulant material is a biomolecule and is added for about 30 min to 4 hours. Typically, a coupling agent is not added. The pH depends, at least in part, on the biomolecule used and can range from about 5 through 11.

The SERS active composite nanostructure can be attached to a probe molecule. The SERS active composite nanostructure can be attached to a structure (e.g., in an assay) or float freely (e.g., in a microfluidic system or in flow cytometry). The probe molecule can be any molecule capable of being linked to the SERS active composite nanostructure either directly or indirectly via a linker. The probe molecule can be attached to the SERS active composite nanostructure by a stable physical and/or chemical association.

The probe molecule has an affinity for one or more target molecules for which detection is desired. If, for example, the target molecule is a nucleic acid sequence, the probe molecule should be chosen so as to be substantially complementary to the target molecule sequence, such that the hybridization of the target and the probe occurs. The term "substantially complementary," means that the probe molecules are sufficiently complementary to the target sequences to hybridize under the selected reaction conditions.

Preferably, the probe molecule and the target molecule are polypeptides (e.g., protein such as, but not limited to an antibody (monoclonal or polyclonal)), nucleic acids (both monomeric and oligomeric), polysaccharides, sugars, fatty acids, steroids, purines, pyrimidines, drugs, ligands, or combinations thereof.

Use of the phrase "polypeptide" or "protein" is intended to encompass a protein, a glycoprotein, a polypeptide, a peptide, and the like, whether isolated from nature, of viral, bacterial, plant, or animal (e.g., mammalian, such as human) origin, or synthetic, and fragments thereof. A preferred protein or fragment thereof includes, but is not limited to, an antigen, an epitope of an antigen, an antibody, or an antigenically reactive fragment of an antibody.

Use of the phrase "nucleic acid" is intended to encompass DNA and RNA, whether isolated from nature, of viral, bacterial, plant or animal (e.g., mammalian, such as human) origin, synthetic, single-stranded, double-stranded, comprising naturally or non-naturally occurring nucleotides, or chemically modified.

The present disclosure provides a method of detecting one or more target molecules in a sample. The method includes attaching a target molecule (e.g., via a probe molecule) to the nanostructure and measuring the SERS spectrum of the nanostructure, where the detection of SERS spectrum specific for the reporter molecule indicates the presence of the target molecule specific for the probe molecule. The SERS active composite nanostructure can be used to detect the presence of one or more target molecules in chemical array systems and biomolecular array systems. In addition, SERS active composite nanostructures can be used to enhance encoding and multiplexing capabilities in various types of systems.

In one embodiment, a flow cytometer can be used in multiplexed assay procedures for detecting one or more target molecules using one or more SERS active composite nanostructure. Flow cytometry is an optical technique that analyzes particular particles (e.g., SERS active composite nanostructures) in a fluid mixture based on the particles' optical characteristics. Flow cytometers hydrodynamically focus a fluid suspension of SERS active composite nanostructures into a thin stream so that the SERS active composite nanostructures flow down the stream in substantially single file and pass through an examination zone. A focused light beam, such as a laser beam, illuminates the SERS active composite nanostructures as they flow through the examination zone. Optical detectors within the flow cytometer measure certain characteristics of the light as it interacts with the SERS active composite nanostructures. Commonly used flow cytometers can measure SERS active composite nanostructure emission at one or more wavelengths.

One or more target molecules can be detected using a SERS active composite nanostructure and one or more probes having an affinity for one or more of the target molecules. Each SERS active composite nanostructure has a reporter molecule that corresponds to the probe. Prior to being introduced to the flow cytometer, the SERS active composite nanostructures specific for certain target molecules are mixed with a sample that may include one or more target molecules. The SERS active composite nanostructures interact with (e.g., bond or hybridize) the corresponding target molecules for which the probe has an affinity.

Next, the SERS active composite nanostructures are introduced to the flow cytometer. As discussed above, the flow cytometer is capable of detecting the SERS active composite nanostructure after exposure to a first energy. Detection of a certain Raman spectrum corresponding to a certain reporter molecule indicates that a target molecule is present in the sample.

EXAMPLE 1

Now having described the embodiments of the nanostructure in general, Example 1 describes some embodiments of the SERS active composite nanostructure which are described in Doering and Nie, *Anal. Chem.*, 2003, 75, 6171-6176 and in William Doering's Dissertation entitled "Mechanisms and Applications of Single-Nanoparticle Surface-Enhanced Raman Scattering," Chapters 3-5, Indiana University—Bloomington, August, 2003. While embodiments of nanostructures are described in connection with Example 1 and the corresponding text and figures, there is no intent to limit embodiments of the nanostructures to these descriptions. On the contrary, the intent is to cover all alternatives, modifications, and equivalents included within the spirit and scope of embodiments of the present disclosure.

In this Example, a class of core-shell colloidal nanoparticles (e.g., SERS active composite nanostructures) that are highly efficient for SERS and are suitable for multiplexed detection and spectroscopy at the single-particle level are disclosed. The SERS active composite nanostructures contain a metallic core for optical enhancement, a reporter molecule for spectroscopic signature, and an encapsulating silica shell for protection and conjugation. With nearly optimized gold cores and silica shells, the SERS active composite nanostructures are stable in both aqueous electrolytes and organic solvents, yielding intense single-particle SERS spectra. Blinking or intensity fluctuation is still observed, indicating that the SERS signals could arise from single molecules at the interface between the core and the shell. A surprising finding is that organic dyes with an isothiocyanate (—N=C=S) group or multiple sulfur atoms are compatible with the silica encapsulation process, and are an excellent group of Raman reporters due to their rich vibrational spectra and the possibility of combined surface enhancement and resonance enhancement.

In contrast to most previous SERS studies, the surface enhanced Raman signals reported here do not come from the target molecules, but from a reporter dye that is embedded in the SERS active composite nanostructures. This design avoids the problems of, among other things, surface adsorption, substrate variations, and poor data reproducibility. This development has opened new possibilities in using SERS for spectroscopic labeling of multiple biomarkers in single cells and tissue specimens, including Raman-activated flow cytometry and cell sorting. In comparison with other biolabels such as fluorescent dyes and semiconductor quantum dots, SERS active composite nanostructures contain a built-in mechanism for signal enhancement and provide rich spectroscopic information in ambient conditions. Furthermore, the extremely short lifetimes of Raman scattering prevent photobleaching, energy transfer, or quenching in the excited state.

Experimental Section

Materials: Ultrapure water (18 MΩcm−1) was used to prepare all aqueous solutions. Concentrated nitric acid, concentrated sulfuric acid, hydrogen tetrachloroaurate(III) (99.99%), Amberlite MB-150 (16-50 mesh), tetraethyl orthosilicate (99.999%), 3,3'-diethylthiadicarbocyanine iodide (98%), (3-mercaptopropyl) trimethoxysilane, and sodium silicate solution (27% $SiO_2$ in 14% NaOH) were obtained from Aldrich (Milwaukee, Wis.) and were used as received. The following reagents were also used without further purification: sodium citrate dihydrate (99.9%, EMD Chemicals, Gibbstown, N.J.), concentrated hydrochloric acid(EMD Chemicals), ammonium hydroxide (29.3%, Fisher, Pittsburgh, Pa.), crystal violet (97%, Fisher), sodium hydroxide (50% (w/w), Fisher), malachite green isothiocyanate (Molecular Probes, Eugene, Oreg.), tetramethylrhodamine-5-isothiocyanate (Molecular Probes), X-rhodamine-5-(and-6)-isothiocyanate (Molecular Probes), (3-aminopropyl) trimethoxysilane (APTMS, United Chemical Technologies, Bristol, Pa.), and ethanol (absolute, Aaper Alcohol and Chemical Co., Shelbyville, Ky.).

Synthesis: Gold colloids with a target diameter of about 60 nm were synthesized according to literature procedures. All glassware was cleaned rigorously and rinsed with water prior to use. In a 50 mL glass flask, 30 mL of a 0.01% aqueous solution of $HAuCl_4$ was brought to a boil under magnetic stirring. Upon boiling, 180 µL of 1% sodium citrate was rapidly injected. Within minutes, the pale yellow solution turned deep purple and quickly progressed to red. The colloid was boiled for approximately 15 minutes to ensure complete reduction, was allowed to cool to room temperature, and was reconstituted to 30 mL before use.

To prepare SERS active composite nanostructures with an embedded Raman reporter (i.e., a reporter molecule), about 0.1 g mixed bed ion-exchange resin was stirred with the freshly prepared gold colloid to remove excess ions. The resin was removed either by filtration or careful decanting, and the colloid was diluted with an equal amount of water. A Raman reporter was added under rapid stirring to a concentration not exceeding about $7.5\times10^{-8}$ M and was allowed to equilibrate for about 15 minutes. Next, a coupling agent (3-mercaptopropyl trimethoxysilane or MPTMS) in ethanol was added to a final concentration of about $2.5\times10^{-7}$ M. After about 15 minutes for this coupling agent to adsorb on the gold particles, the pH was adjusted to about 9.5 with 100 mM NaOH. Silica deposition was achieved by using sodium silicate, activated by diluting a stock solution to 0.54% in water and adjusting the pH to 10.8. An aliquot (about 3 mL) of this silicate solution was added to the colloid, and was stirred magnetically for 42 hours.

These conditions favored slow growth of a uniform silica layer and avoided nucleation and formation of pure silica particles. But the shell thickness achieved with this slow growth process was only about 5 nm, too thin to protect colloidal particles from aggregation. Thus, the silica shell was expanded with a precipitation step, in which ethanol was slowly added to condense the remaining silicate onto the existing shell. Pure silica particles formed during this step were readily separated from the encapsulated particles by centrifugation for about 90 minutes at about 1700 g. The silica-coated particles could be re-suspended in various media such as phosphate-buffered saline (PBS), dimethyl sulfoxide (DMSO), ethanol, and acetone.

Measurements: A scanning spectrophotometer (Shimadzu, Columbia, Md.) was used to acquire UV-visible absorption spectra. High-magnification transmission electron micrographs were taken using a Phillips CM200 electron microscope and were recorded on a TVIPS 2k by 2k CCD. Bulk Raman spectra were recorded using a dispersive Raman spectroscopy system (Solution 633, Detection Limit, Laramie, Wyo.). Single-particle spectra were obtained with an inverted optical microscope (Diaphot 200, Nikon, Melville, N.Y.), equipped with a mixed gas argon/krypton ion laser (Lexel 3500, Fremont, Calif.) for 647 nm excitation.

Regions of interest were first screened with wide-field illumination, and Raman-active particles were located with a video-rate intensified. CCD (ICCD, PTI, Inc., Lawrenceville, N.J.) mounted to the front microscope port. Confocal optics was then used to focus on an individual SERS active composite nanostructures, and back-scattered Raman signals were collected through a microscope objective (Plan 100×, oil immersion, NA=1.25). A triple-bandpass filter (Chroma Tech, Brattleboro, Vt.) was used to block the laser line and extraneous signals. Spectroscopic signatures were obtained with a CCD detector (TKB512, Princeton Instruments, Trenton, N.J.) mounted on a single-stage spectrometer (Model 270M, Spex, Edison, N.J.).

Results and Discussion

SERS active composite nanostructures: Several procedures are available for coating colloidal nanoparticles with silica. A coupling agent such as aminopropyl trimethoxysilane (APTMS) is often used to make the particle surface vitreophilic, followed by deposition of a more condensed silica layer. However, because the SERS-active particles require direct adsorption of a reporter on the gold surface, the coupling agent or the silica layer could displace the reporter molecules, causing a loss of the Raman spectroscopic signatures. In fact, the low SERS intensities reported previously for silica-encapsulated gold particles are likely caused by the interference of a silica shell with reporter adsorption. This problem is solved by carefully controlling the reporter and coupling agent concentrations and by using a special class of reporter molecules that are more compatible with silica encapsulation.

Figure 3:
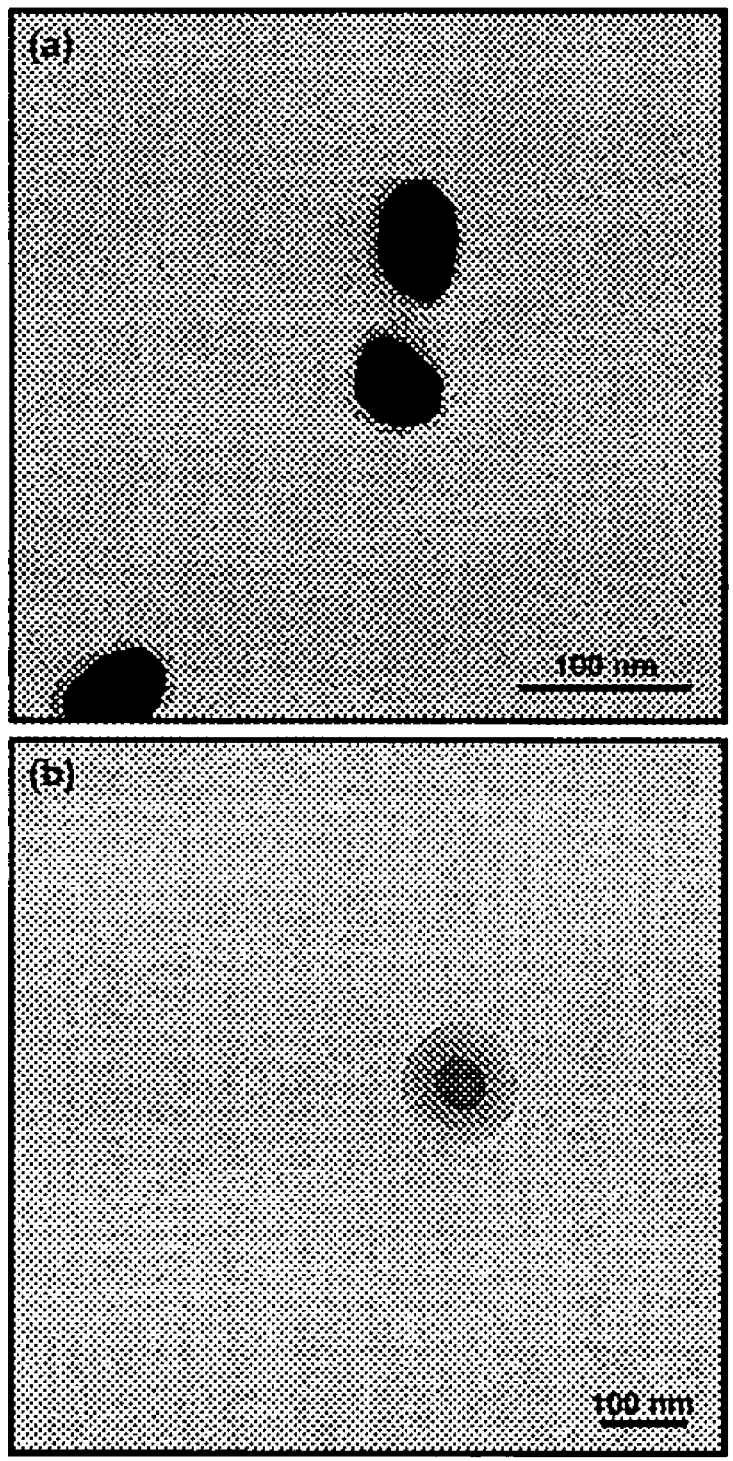
FIG. 3 illustrates the core-shell structure of two representative embodiments of a SERS active composite nanostructure using transmission electron microscopy (TEM), where the upper image has about a 6 nanometer-thick silica shell and the lower image has about a 40 nanometer-thick silica shell.

For example, a reporter molecule is first added to the gold colloid, followed by addition of a silane coupling agent. The reporter concentration ($7.5 \times 10^{-8}$ M, about 20-25% coverage of the particle surface), is low enough to prevent colloid aggregation, but high enough to yield intense SERS signals. The coupling agent concentration ($2.5 \times 10^{-7}$ M) is also controlled so that its maximum surface coverage is about 50%; that is, only about half of the gold surface is covered with the coupling agent. Under these conditions, both the reporter molecule and the coupling agent can co-adsorb on the particle. Previous work has shown that 50% surface coverage by the coupling agent is sufficient to induce the formation of a complete silica shell. Indeed, it was found that a thin silica layer (about nm thick) could be grown uniformly on the particle surface in the presence of activated sodium silicate. This initial shell (often porous) is expanded by silicate precipitation in ethanol, producing a condensed silica layer with a controllable thickness between about 10 to 50 nm. The core-shell nanoparticle structure is confirmed by transmission electron microscopy for both thin and thick shells (FIG. 3). The thin silica layer has a rough and irregular morphology, while the thick shell is smooth and dense. In fact, it has been reported that increased silica deposition leads to spherical and nearly monodisperse particles, regardless of the shape and size of the original gold colloids.

Figure 4:
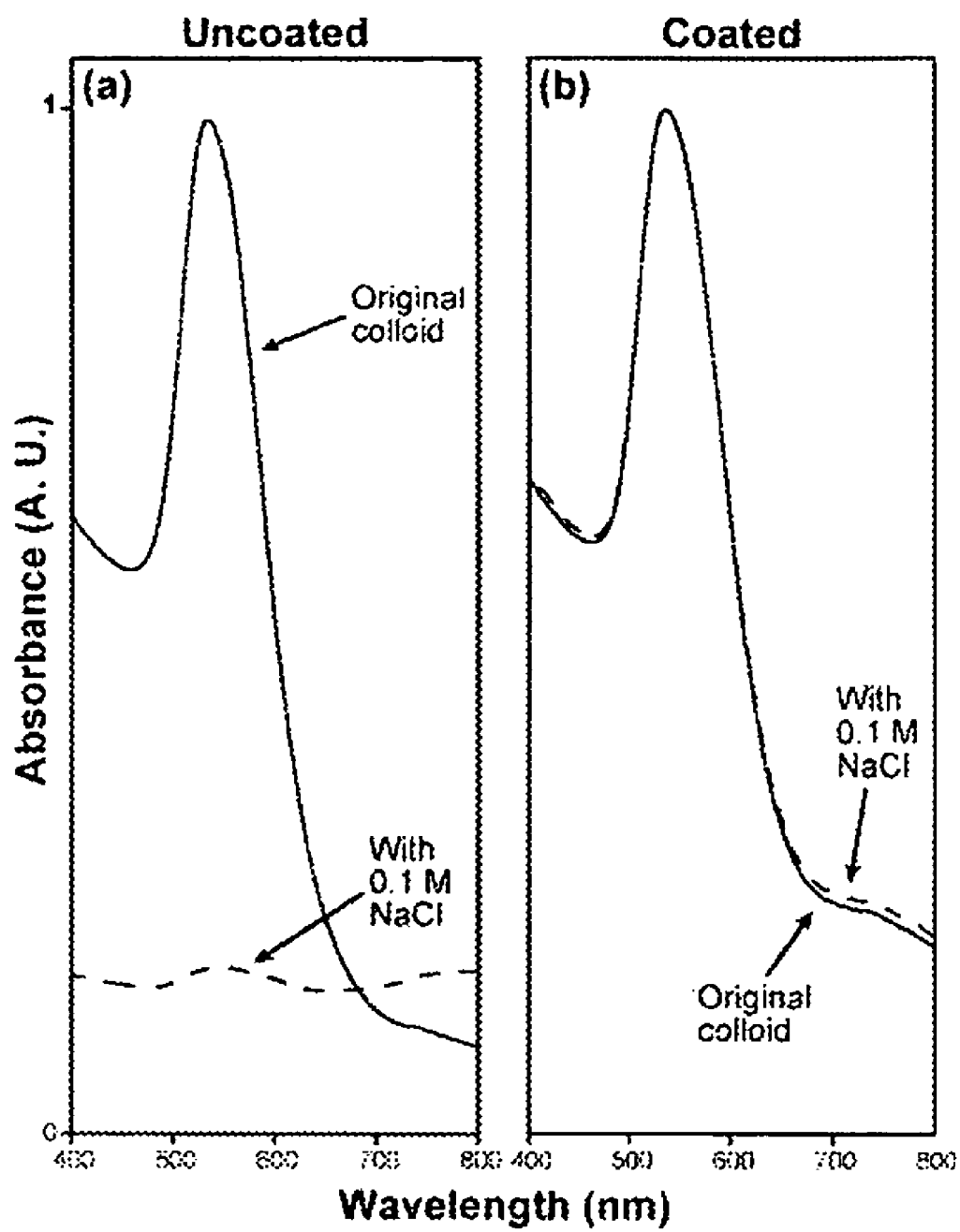
FIG. 4 illustrates absorption spectra of a representative embodiment of a SERS-active composite nanostructure and an uncoated gold nanoparticle. In particular.

One feature of exemplary SERS active composite nanostructures is their remarkable stability in comparison with the uncoated colloids. As depicted in FIG. 4, absorption spectra of the SERS active composite nanostructures (b) show little or no changes upon the addition of 100 mM sodium chloride, where as the uncoated colloids (a) are completely aggregated and precipitated. Furthermore, the SERS active composite nanostructures are stable in organic solvents such as methanol and acetone that are known to precipitate protein-stabilized gold colloids. Even after long-term storage (about 18-20 months) in aqueous or organic solution, the SERS active composite nanostructures maintained their original SERS activity and showed no aggregation.

Silica coating causes a red shift (longer wavelength or lower energy) in the surface plasmon absorption spectra of colloidal gold, in agreement with previous results. This shift is believed to occur because the plasmon resonance frequencies are dependent on the refractive index of the surrounding medium and because silica has a higher refractive index (n=1.57) than water (n=1.33). UV-visible absorption spectra obtained at various stages of silica deposition indicate that the wavelength shift is a function of the silica shell thickness (data not shown). A consistent shell is observed with various Raman reporters, indicating that silica deposition is not affected by reporter adsorption.

Figure 5:
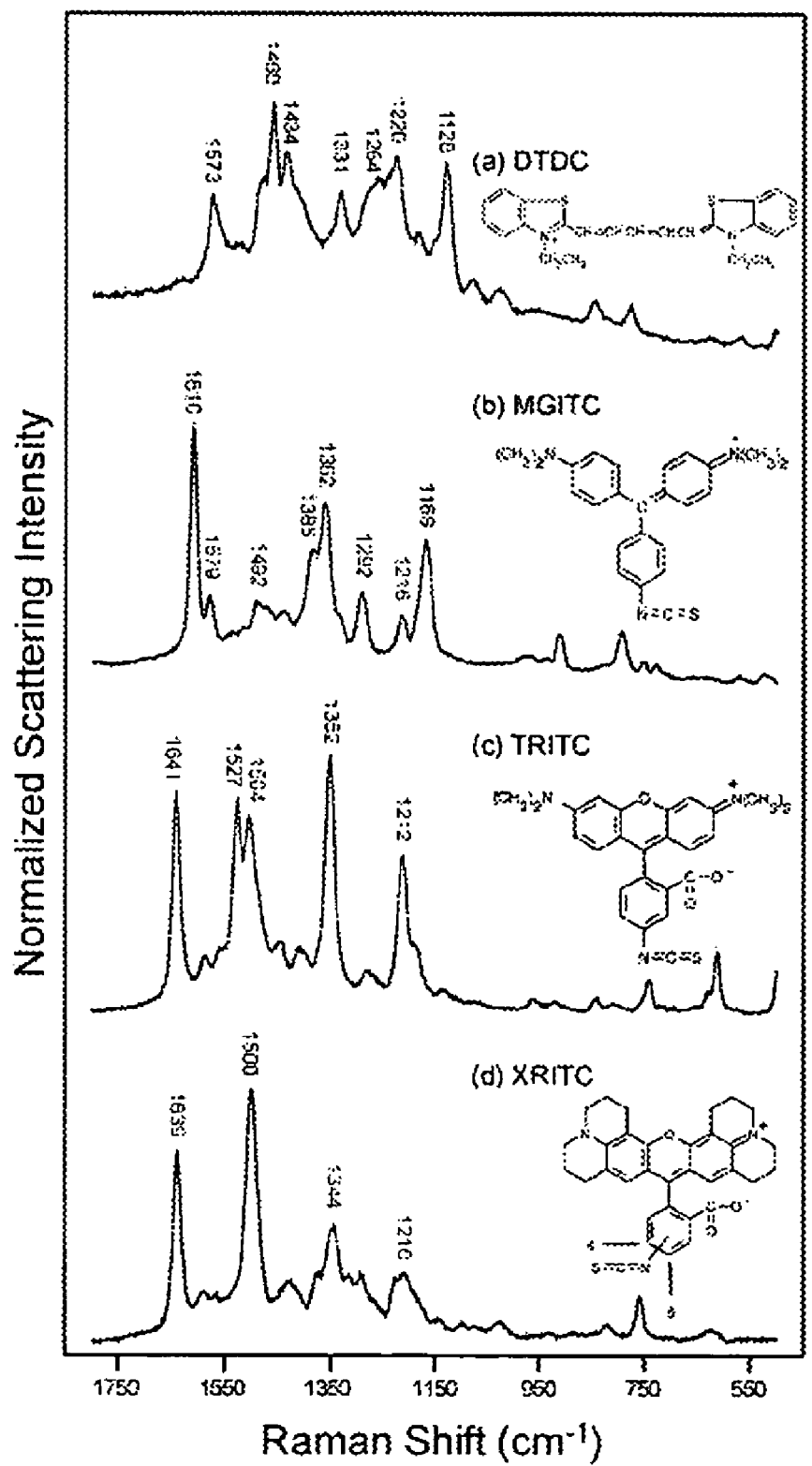
FIG. 5 illustrates surface-enhanced resonance Raman spectra for SERS-active composite nanostructures having the following reporter molecules: (a) malachite green isothiocyanate (MGITC), (b) tetramethylrhodamine-5-isothiocyanate (TRITC), (c) X-rhodamine-5-(and-6)-isothiocyanate (XRITC), and (d) 3,3'-diethylthiadicarbocyanine iodide (DTDC).

Raman Reporters: Small organic compounds such as thiophenol, mercaptobenzoic acid, and bispyridine were previously used as Raman spectroscopic reporters. These molecules give rise to simple Raman spectra, but it has been difficult or impossible to achieve resonance Raman enhancement at visible excitation wavelengths. As a result, the reported SERS intensities are relatively low, even at high (millimolar) reporter concentrations. To address this problem, a broad range of organic compounds with various functional groups for potential use as Raman reporters have been examined in this Example. The result reveals that organic dyes with an isothiocyanate (—N═C═S) group or with multiple sulfur atoms adsorb strongly on the core particles and are compatible with silica encapsulation. For example, intense SERS spectra have been obtained from (b) malachite green isothiocyanate (MGITC), (c) tetramethylrhodamine-5-isothiocyanate TRITC), (d) X-rhodamine-5-(and-6)-isothiocyanate (XRITC), and (a) 3,3'-diethylthiadicarbocyanine iodide (DTDC) (FIG. 5). Three of these molecules contain an isothiocyanate group, while the fourth has two sulfur atoms in ring structures.

The isothiocyanate group or sulfur atoms provide an "affinity tag" for binding to gold surfaces, yielding a sulfur-gold bond that is stable against the coupling agent and silica deposition. For molecules without such an affinity tag such as crystal violet and rhodamine 6G, intense SERS spectra was observed, but the signals disappeared after silica coating. In addition, most of these dyes have strong electronic transitions in the visible spectrum, so resonance Raman enhancement can be used to further increase the signal intensities. In a strict sense, these molecules should be called "resonant Raman reporters," to distinguish them from thiophenol and other nonresonant Raman reporters. In most cases, resonance Raman provides about 2-3 orders of magnitude of additional enhancement relative to surface enhancement alone. Both fluorescent and nonfluorescent dyes can be used as resonant Raman reporters because fluorescence emission is efficiently quenched by the gold particles, not interfering with Raman measurement. A series of benzotriazole dyes are excellent for surface-enhanced resonance Raman scattering; due to the presence of multiple nitrogen atoms, these molecules could provide a new class of resonant Raman reporters for spectroscopic encoding and multiplexing applications.

Figure 6:
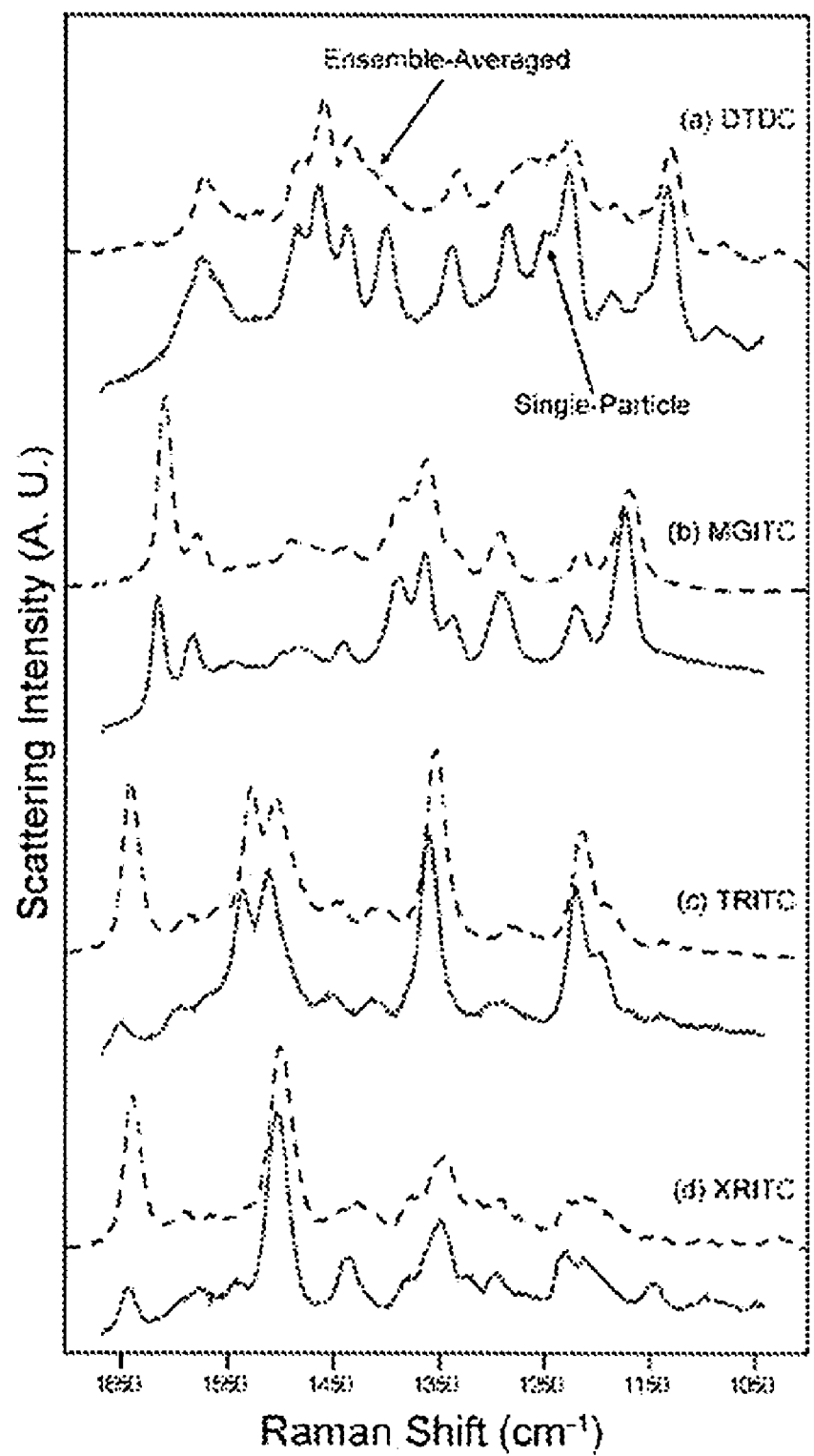
FIG. 6 illustrates ensemble-averaged (black dotted curves) and single-particle (solid curves) surface-enhanced resonance Raman scattering spectra obtained for silica-coated gold SERS active composite nanostructures, each embedded with a distinct reporter molecule (a) through (d). The core diameter is about 60 nanometers and the core is coated with a 15-nanometer-thick silica shell.

Single-Particle SERS: Under nearly optimized conditions, the uncoated and coated gold nanoparticles show similar surface-enhanced resonance Raman scattering (SERRS) intensities, with total enhancement factors on the order of $10^{13}$-$10^{14}$. These values represent the total enhancement factors of surface enhancement and resonance enhancement, and are calculated by dividing the SERS cross sections of crystal violet by the normal Raman cross sections of methanol. Intense SERRS spectra can be obtained from both single uncoated and single coated particles, with the fractions of optically "hot" or SERS-active particles approaching 30-50%. In comparison with bulk or ensemble-averaged data, the single-particle spectra are considerably better resolved (FIG. 6). There are also differences in the relative intensities or spectral patterns, but these differences are primarily caused by instrumental artifacts. Two different instruments were used to obtain the bulk and single-particle data, but these two systems have very different spectral responses (primarily due to the use of optical filters).

Figure 7:
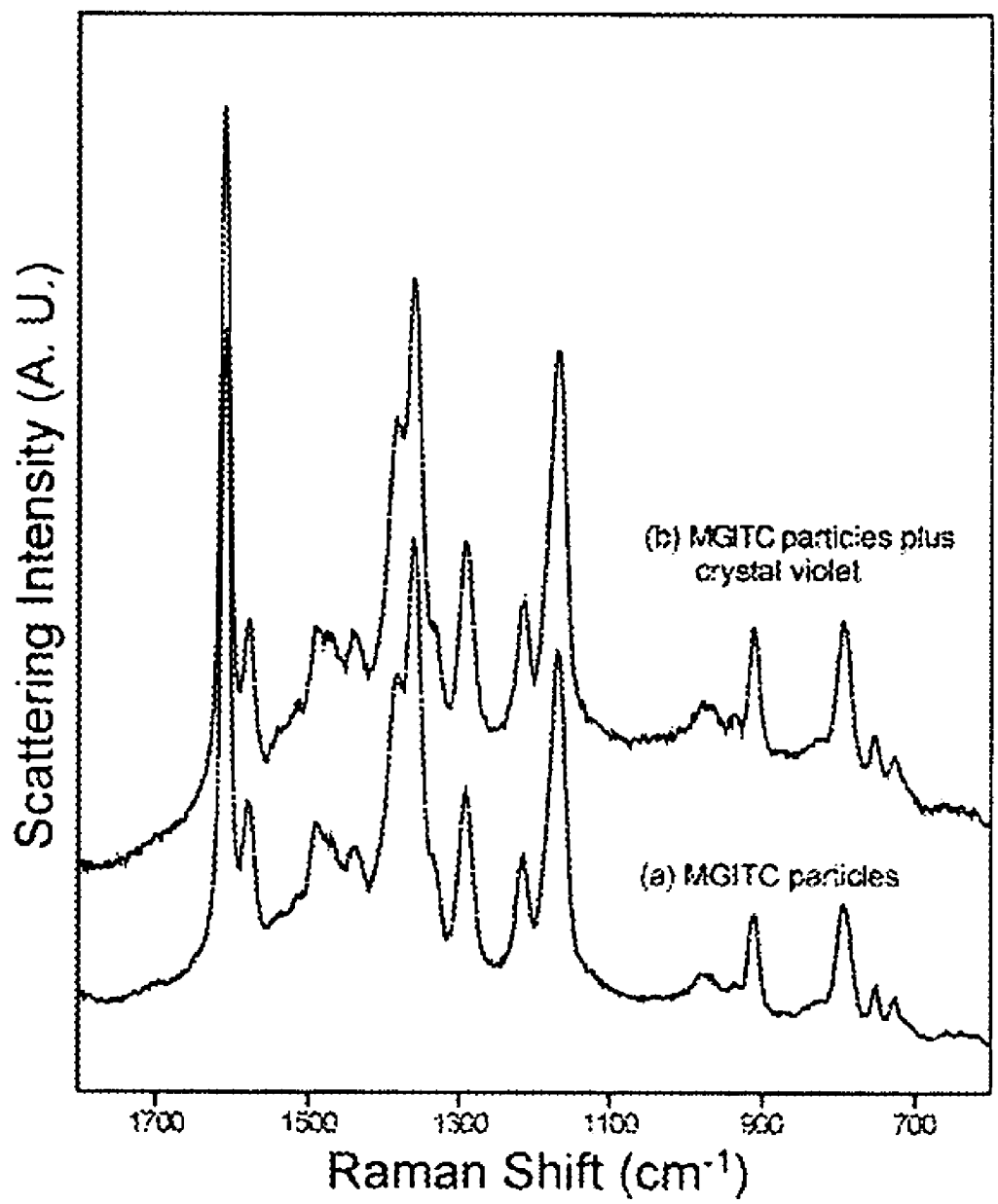
FIG. 7 illustrates surface-enhanced resonance Raman scattering spectra for silica-coated MGITC gold SERS active composite nanostructures (FIG. 6) before (a) and after (b) the addition of excess crystal violet (1 mM).

Reporter molecules can not move out of the particle and external molecules can not compete for adsorption on the core. In particular, although small ions can penetrate a porous silica shell, larger molecules appear to be blocked. FIG. 7 shows SERS data obtained from a competitive adsorption experiment in which concentrated crystal violet was added to gold colloids that were pre-embedded with malachite green. A comparison of the two spectra (with and without crystal violet added) shows no change in the malachite green spectrum and no SERS signals from crystal violet. The only difference appears to be a higher background, similar to the background of crystal violet in pure water. This result conclusively shows that the Raman reporters are "locked in," while external molecules are "locked out."

Previous research has shown that spatially isolated, single gold particles emit Stokes-shifted Raman photons in an intermittent on and off fashion. A similar behavior has been noted also for single fluorescent molecules and single quantum dots. While the true origins of this behavior are still under debate, recent studies suggest diffusion of single molecules on the particle surface or at the junction of two particles as a major cause. It is thus interesting that the silica-coated nanoparticles still show blinking, although one would expect a silica layer to prevent or reduce diffusion at the core-shell interface. This observation suggests that the SERS signals could originate from a single reporter molecule adsorbed at an active site on the gold core. Quantitative analysis indicates that there should be many reporter molecules on each particle, but the SERS signals are often dominated by a single or a few molecules. As reported in previous papers, this single-molecule behavior under "many-molecule" conditions is likely to arise from the molecular dimensions of the active sites, which could only accommodate a single or a few molecules.

In conclusion, a class of Raman spectroscopic tags by using dye-embedded colloidal nanoparticles (SERS active composite nanostructures) and SERS has been developed. The SERS active composite nanostructures have a core-shell structure containing a metal core, a reporter molecule, and silica coating. The reactive isothiocyanate group or multiple sulfur atoms can be used as "molecular anchors" for embedding organic dyes into core-shell particles. The SERS active composite nanostructures are stable in both aqueous electrolytes and organic solvents. The achieved enhancement factors are on the order of $10^{13}$-$10^{14}$, large enough for single-particle or even single-molecule spectroscopy. By using gold colloids, highly monodispersed particles can be prepared with simple procedures. In comparison with other biological labels, SERS active composite nanostructures provide high sensitivity and spectroscopic information, two features that enable multiplexed analysis of molecular biomarkers and multi-parameter flow cytometry.

It should be emphasized that the above-described embodiments of the present disclosure, particularly, any "preferred" embodiments, are merely possible examples of implementations, and are merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

The invention claimed is:

1. A nanostructure, comprising:
a surface-enhanced Raman spectroscopic active composite nanostructure comprising:
a core;
at least one reporter molecule bonded to the core, wherein the reporter molecule is selected from malachite green isothiocyanate, tetramethylrhodamine-5-isothiocyante, X-rhodamine-5-isothiocyanate, X-rhodamine-6-isothiocyanate, and combinations thereof; and
an encapsulating material disposed over the core and the reporter molecule, wherein after encapsulation with the encapsulating material the reporter molecule has a measurable surface-enhanced Raman spectroscopic signature.

2. The nanostructure of claim 1, wherein the core is gold.

3. The nanostructure of claim 1, wherein the core is selected from gold, silver, copper, sodium, aluminum, chromium, and combinations thereof.

4. The nanostructure of claim 1, wherein the core has a diameter less than about 200 nanometers.

5. The nanostructure of claim 1, wherein the encapsulating material is selected from silica, polymers, metal oxides, metal sulfides, proteins, peptides, and combinations thereof.

6. The nanostructure of claim 1, wherein the encapsulating material is silica.

7. The nanostructure of claim 1, wherein the encapsulating material has a diameter less than about 50 nanometers.

8. The nanostructure of claim 1, wherein the reporter molecule covers about 1 to 75% of the surface of the core.

9. The nanostructure of claim 1, wherein the surface-enhanced Raman spectroscopic active composite nanostructure is incorporated into a system selected from a cytometry system, a chemical array system, a biomolecule array system, a biosensing system, a biolabeling system, a high-speed screening system, a gene expression system, a protein expression system, a medical diagnostic system, a diagnostic library, and a microfluidic system.

10. A surface-enhanced Raman spectroscopic active composite nanostructure, comprising:
a core;
at least one reporter molecule disposed on the core, wherein the reporter molecule covers about 15 to 50% of the surface of the core; and
an encapsulating material covers the core and the reporter molecule, wherein after encapsulation with the encapsulating material the reporter molecule has a measurable surface-enhanced Raman spectroscopic signature.

11. The nanostructure of claim 10, wherein the reporter molecule is selected from malachite green isothiocyanate, tetramethylrhodamine-5-isothiocyante, X-rhodamine-5-isothiocyanate, X-rhodamine-6-isothiocyanate and combinations thereof.

12. The nanostructure of claim 10, wherein the core is gold; the reporter molecule is selected from malachite green isothiocyanate, tetramethylrhodamine-5-isothiocyante, X-rhodamine-5-isothiocyanate, and X-rhodamine-6-isothiocyanate; and the encapsulating material is silica.

13. The nanostructure of claim 10, further comprising a coupling agent bonded to the core.

14. The nanostructure of claim 12, wherein the coupling agent covers about 40 to 60% of the surface of the core.

15. A method of preparing a nanostructure, comprising:
introducing the core to a reporter molecule, wherein the reporter molecule bonds to the core, wherein the reporter molecule is selected from an isothiocyanate dye, and combinations thereof; and
disposing an encapsulating material onto the core and reporter molecule, wherein after disposing the encapsulating material, the reporter molecule has a measurable surface-enhanced Raman spectroscopic signature.

16. The method of claim 15, further comprising:
introducing the reporter molecule in an amount so that the reporter molecule covers about 1 to 75% of the surface of the core.

17. The method of claim 16, further comprising:
introducing a coupling agent to the core having at least one reporter molecule bonded thereto, wherein the coupling agent bonds to an uncovered portion of the core.

18. A method of detecting at least one target molecule, comprising:
attaching a target molecule to the nanostructure wherein the nanostructure is comprising:
a surface-enhanced Raman spectroscopic active composite nanostructure comprising:
a core;
at least one reporter molecule bonded to the core, wherein the reporter molecule is selected from malachite green isothiocyanate, tetramethylrhodamine-5-isothiocyante, X-rhodamine-5-isothiocyanate, X-rhodamine-6-isothiocyanate, and combinations thereof; and
an encapsulating material disposed over the core and the reporter molecule, wherein after encapsulation with the encapsulating material the reporter molecule has a measurable surface-enhanced Raman spectroscopic signature;
exciting the reporter molecule with a source of radiation; and
measuring the surface enhanced Raman spectroscopy spectrum of the nanostructure corresponding to the reporter molecule to determine the presence of the target molecule.

19. The method of claim 18, wherein the molecule comprises a biomolecule.

20. The method of claim 18, wherein the reporter molecule is a resonant Raman reporter molecule and further comprising:
measuring the surface enhanced resonant Raman spectroscopy spectrum of the nanostructure corresponding to the reporter molecule to determine the presence of the target molecule.

21. The nanostructure of claim 1, wherein the reporter molecule is malachite green isothiocyanate.

22. The nanostructure of claim 1, wherein the reporter molecule is tetramethylrhodamine-5-isothiocyante.

23. The nanostructure of claim 1, wherein the reporter molecule is X-rhodamine-5-isothiocyanate.

24. The nanostructure of claim 1, wherein the reporter molecule is X-rhodamine-6-isothiocyanate.

* * * * *

UNITED STATES PATENT AND TRADEMARK OFFICE
CERTIFICATE OF CORRECTION

PATENT NO. : 7,588,827 B2
APPLICATION NO. : 10/919944
DATED : September 15, 2009
INVENTOR(S) : Nie et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 963 days.

Signed and Sealed this

Fourteenth Day of December, 2010

David J. Kappos
*Director of the United States Patent and Trademark Office*